United States Patent
Chang et al.

(10) Patent No.: US 12,329,820 B2
(45) Date of Patent: Jun. 17, 2025

(54) CROSS-LINKED SHEAR THINNING FLUID WITH TUNABLE RHEOLOGY FOR 3D BIOPRINTING AND DRUG DELIVERY

(71) Applicant: CORNING INCORPORATED, Corning, NY (US)

(72) Inventors: Theresa Chang, Painted Post, NY (US); Huayun Deng, Painted Post, NY (US); Benjamin Leonard Linchuck, Charlotte, NC (US); Ying Wei, Painted Post, NY (US); Ying Zhang, Horseheads, NY (US); Yue Zhou, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 1134 days.

(21) Appl. No.: 16/611,015

(22) PCT Filed: May 7, 2018

(86) PCT No.: PCT/US2018/031290
§ 371 (c)(1),
(2) Date: Nov. 5, 2019

(87) PCT Pub. No.: WO2018/208632
PCT Pub. Date: Nov. 15, 2018

(65) Prior Publication Data
US 2020/0061193 A1 Feb. 27, 2020

Related U.S. Application Data

(60) Provisional application No. 62/505,353, filed on May 12, 2017.

(51) Int. Cl.
*A61K 47/36* (2006.01)
*A61K 45/06* (2006.01)
*C08B 37/00* (2006.01)

(52) U.S. Cl.
CPC .......... *A61K 47/36* (2013.01); *C08B 37/0045* (2013.01); *A61K 45/06* (2013.01)

(58) Field of Classification Search
CPC ..... A61K 47/36; A61K 45/06; C08B 37/0045
See application file for complete search history.

(56) References Cited

U.S. PATENT DOCUMENTS

| | | | |
|---|---|---|---|
| 5,929,051 A | 7/1999 | Ni et al. | |
| 6,251,424 B1 * | 6/2001 | Al-Lamee | A61L 26/008 424/443 |
| 6,274,548 B1 | 8/2001 | Ni et al. | |
| 6,407,226 B1 | 6/2002 | Simensen et al. | |
| 6,777,000 B2 | 8/2004 | Ni et al. | |
| 9,006,213 B2 | 4/2015 | Cohen et al. | |
| 2003/0134027 A1 | 7/2003 | Te Hennepe et al. | |
| 2012/0089238 A1 | 4/2012 | Kang et al. | |
| 2014/0019927 A1 | 1/2014 | Yudhistira et al. | |
| 2015/0202299 A1 | 7/2015 | Burdick et al. | |
| 2016/0136895 A1 | 5/2016 | Beyer et al. | |
| 2016/0145567 A1 | 5/2016 | Henry et al. | |
| 2016/0145600 A1 | 5/2016 | Caracci et al. | |
| 2018/0171304 A1 | 6/2018 | Beyer et al. | |

FOREIGN PATENT DOCUMENTS

| | | |
|---|---|---|
| JP | 01-240155 A | 9/1989 |
| JP | 2002-501406 A | 1/2002 |
| JP | 2002-047128 A | 2/2002 |
| JP | 2004-231566 A | 8/2004 |
| JP | 2005-513079 A | 5/2005 |
| JP | 2009-067790 A | 4/2009 |
| WO | 9730092 A2 | 8/1997 |
| WO | 9959542 A1 | 11/1999 |
| WO | 2014/197999 A1 | 12/2014 |
| WO | 2016/201577 A1 | 12/2016 |

OTHER PUBLICATIONS

Derby; "Printing and Prototyping of Tissues and Scaffolds"; Science, vol. 338 (2012) pp. 921-926.
Hockaday et al; "Rapid 3D Printing of Anatomically Accurate and Mechanically Heterogeneous Aortic Valve Hydrogel Scaffolds"; Biofabrication. 4 (3); (2012) 22 Pages.
International Search Report and Written Opinion of the International Searching Authority; PCT/US2018/031290; Mailed Aug. 6, 2018; 10 Pages; European Patent Office.
Lee et al; "Creating Perfused Functional Vascular Channels Using 3D Bio-Printing Technology"; Biomaterials, 35 (2014) pp. 8092-8102.
Malda et al; "25th Anniversay Article: Engineering Hydrogels for Biofabrication"; Adv. Mater. 2013, 25, pp. 5011-5028.
Japanese Patent Application No. 2019-562315, Office Action, dated Mar. 16, 2022, 08 pages (04 pages of English Translation and 04 pages of Original Copy); Japanese Patent Office.

\* cited by examiner

*Primary Examiner* — Genevieve S Alley
(74) *Attorney, Agent, or Firm* — Chandra J. Duncan (57) ABSTRACT

Cross-linked shear-thinning fluids of pectic acid demonstrating increased viscosity with decreasing shear, as well as methods of producing and using the same. A shear-thinning fluid includes an aqueous solution of pectic acid cross-linked by a divalent cation is disclosed. The pectic acid may be present in an amount ranging from about 0.5 to about 3.0% (w/v), the divalent cation may be present at a concentration of from about 0.5 mM to about 7.0 mM, and the viscosity of the shear-thinning fluid increases with decreasing shear. These cross-linked shear-thinning fluids of pectic acid can be utilized for controlled release formulations, cell encapsulation, and 3D printing, and provide for an improved balance between structure fidelity/mechanical stability and cell viability.

19 Claims, 5 Drawing Sheets

CROSS-LINKED SHEAR THINNING FLUID WITH TUNABLE RHEOLOGY FOR 3D BIOPRINTING AND DRUG DELIVERY

CROSS REFERENCE TO RELATED APPLICATION

This is a national stage application under 35 U.S.C. § 371 of International Application No. PCT/US2018/031290, filed May 7, 2018, which claims the benefit of priority of U.S. Provisional Application Ser. No. 62/505,353 filed on May 12, 2017 the contents of which are relied upon and incorporated herein by reference in their entirety.

BACKGROUND

Field

The present disclosure generally relates to cross-linked shear-thinning fluids of pectic acid having tunable rheology and displaying increased viscosity with decreasing shear for improved structure fidelity and mechanical stability, as well as to methods of producing and using the same.

Technical Background

Figure 1:
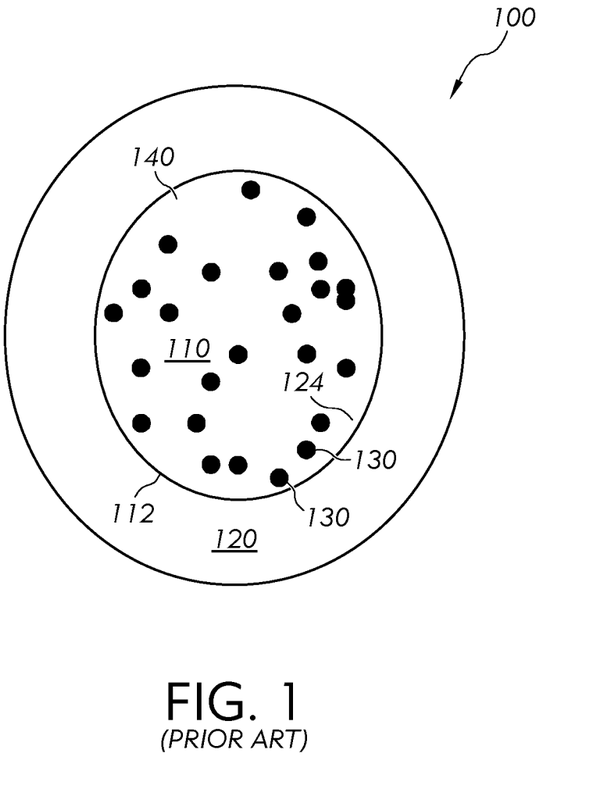
FIG. 1 is a schematic diagram of a magnetic microcarrier having a cross-linked hydrogel of alginate or pectate in the prior art.

Cross-linked polymer gel materials, including cross-linked hydrogels, have broad application and potential in the biomedical industry. Such gel materials are being explored and utilized for producing tissue engineering scaffolds through 3D printing, a form of additive manufacturing. Ideally, systems for printing 3D structures include the direct printing of cellular materials; as such systems allow cells to be directly deposited within the 3D scaffold. Additionally, such gel materials are currently being investigated and utilized for controlled release formulations and for cell encapsulation to enhance drug and cell therapies by modulating encapsulated drug and cell activity. A prior art magnetic microcarrier comprising a cross-linked hydrogel of alginate or pectate is shown schematically in FIG. 1. The prior art microcarrier bead 100 includes a composite core 110 and a coating 120 that completely surrounds and encapsulates the core. The composite core 110 comprises a unitary body defining an outer surface 112. The coating 120 is in direct physical contact with the outer surface 112 of the core 110. The composite core 110 is a mixture that comprises one or more particles 130 of a polycrystalline, inorganic magnetic material dispersed throughout a polymer matrix 140. The polymer matrix 140 within the core 110 comprises an indigestible or un-dissolvable polymer material or a mixture of such polymer materials. The coating 120 may comprise a cross-linked hydrogel of alginate or pectate.

However, the development of certain gel materials for use in controlled release formulations, cell encapsulation, and 3D printing focused on mechanical structure and shape fidelity of the gel material at the expense of cell viability. For example, the shear force involved with injecting such gel materials or the shear force involved with propelling droplets of such gel materials onto a substrate during 3D printing often results in damage to cells dispersed in such gel materials. Conversely, the development of alternative gel materials for use in control release formulations, cell encapsulation, and 3D printing emphasized cell viability over mechanical structure and shape fidelity of the material. Such materials are often cross-linked or otherwise solidified after injection or dispensing during 3D printing. However, such injectable gel materials are known to suffer instability after delivery. Similarly, such gel materials lead to a lack of control of the geometry and the cellular and matrix composition of a printed structure, which is due to the temporal delay between printing deposition and the cross-linking steps needed to provide the appropriate shape fidelity of the gel material.

Accordingly, on-going need exists for alternative materials and methods of producing the same that can be utilized for controlled release formulations, cell encapsulation, and 3D printing.

SUMMARY

The embodiments disclosed herein relate to cross-linked shear-thinning fluids of pectic acid having tunable rheology and demonstrating increased viscosity with decreasing shear, as well as methods of producing and using the same. These cross-linked shear-thinning fluids of pectic acid can be utilized for controlled release formulations, cell encapsulation, and 3D printing. Due to the high responses to shear thinning and rapid recovery back into stable, highly viscous fluids upon shear stress removal, these cross-linked shear-thinning fluids of pectic acid can provide for an improved balance between structure fidelity/mechanical stability and cell viability.

In embodiments, a shear-thinning fluid that includes an aqueous solution of pectic acid cross-linked by a divalent cation is disclosed. The pectic acid may be present in an amount ranging from about 0.5 to about 3.0% (w/v) and the divalent cation may be present at a concentration of from about 0.5 mM to about 7.0 mM. The viscosity of the shear-thinning fluid of pectic acid cross-linked by a divalent cation increases with decreasing shear.

In other embodiments, a method of producing a cross-linked shear-thinning fluid that displays increased viscosity with decreasing shear is disclosed. The method includes providing an aqueous solution of a pectic acid and a divalent cation. The pectic acid may be present in an amount ranging from about 0.5 to about 3.0% (w/v) and the divalent cation may be present in concentration from 0.5 mM to about 7.0 mM. The method further includes mixing the aqueous solution under conditions suitable for cross-linking the pectic acid with the divalent cations to thereby produce the cross-linked shear-thinning fluid that displays increased viscosity with decreasing shear.

It is to be understood that both the foregoing general description and the following detailed description describe various embodiments and are intended to provide an overview or framework for understanding the nature and character of the claimed subject mailer. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

(▲) depicts the steady shear rate sweep of an alginate solution containing 5 mM $CaCO_3$ and 11.2 mM of glucono-delta-lactone (alginate solution formulation #2 of Table 1). (□) depicts the steady shear rate sweep of a pectic acid solution without calcium ions (pectic acid solution formulation #1 of Table 1). (○) depicts the steady shear rate sweep of a pectic acid solution containing 5 mM $CaCO_3$ and 11.2 mM glucono-delta-lactone (pectic acid solution formulation #2 of Table 1).

DETAILED DESCRIPTION

The following description of particular embodiment(s) is merely exemplary in nature and is in no way intended to limit the scope of the present disclosure, its application, or uses, which may, of course, vary. Embodiments of the present disclosure are described with relation to the non-limiting definitions and terminology included herein. These definitions and terminology are not designed to function as a limitation on the scope or practice of the embodiments of the present disclosure but are presented for illustrative and descriptive purposes only. While the compositions and methods are described as using specific materials or a specific order of individual steps, it is appreciated that materials or steps may be interchangeable such that the description of the embodiments of the present disclosure may include multiple parts or steps arranged in many ways as is readily appreciated by one of skill in the art.

The terminology used herein is for describing particular aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It is to be further understood that where descriptions of various embodiments use the term "comprising," and/or "including" those skilled in the art would understand that in some specific instances, an embodiment can be alternatively described using language "consisting essentially of" or "consisting of." The term "or a combination thereof" means a combination including at least one of the foregoing elements.

It should be understood that every numerical range given throughout this specification will include every narrower numerical range that falls within such broader numerical range, as if such narrower numerical ranges were all expressly written herein.

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

Figure 2:
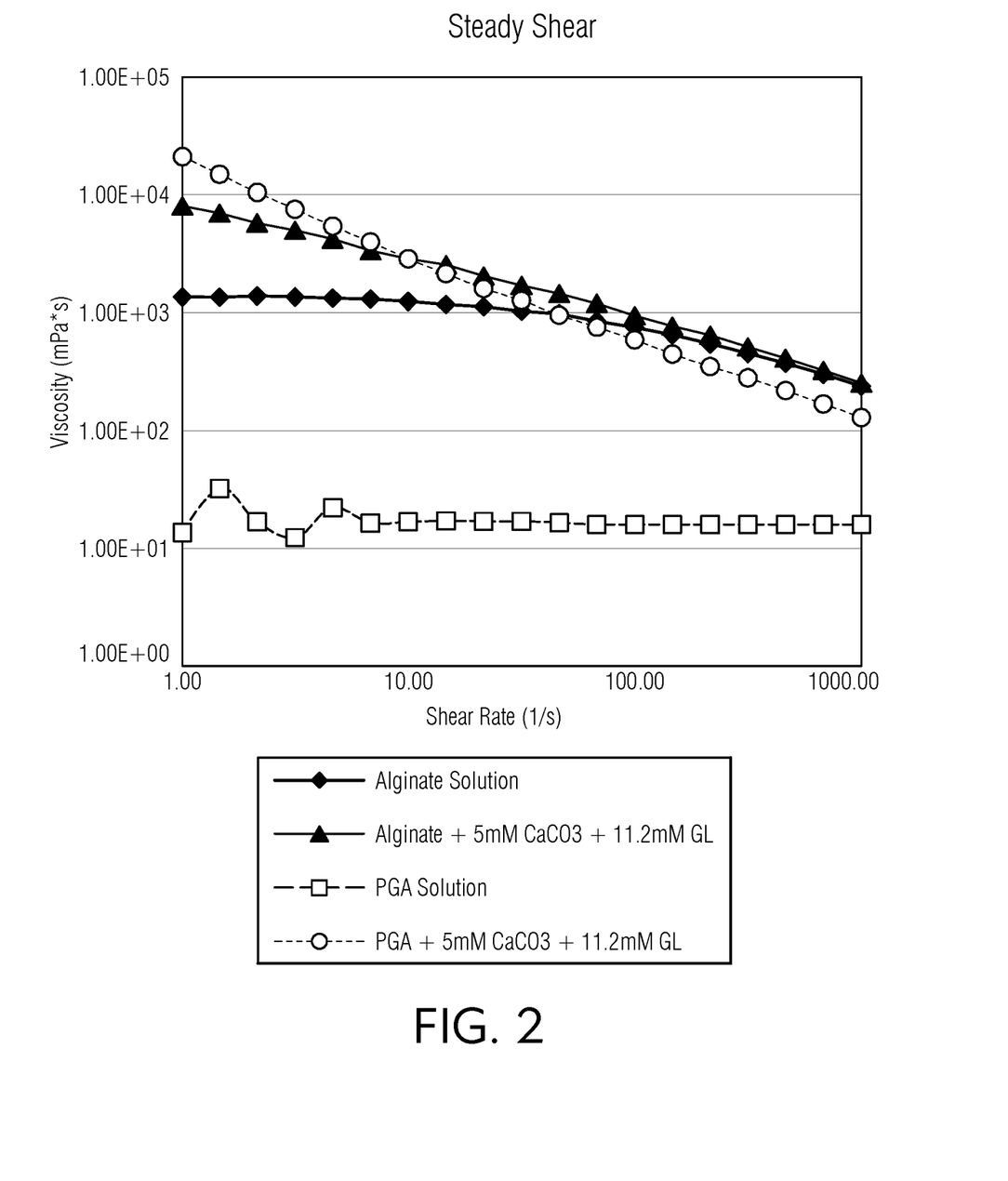
FIG. 2 is a graph depicting the results of steady shear rate sweeps of alginate or pectic acid based solutions with or without a low concentration of calcium ions. (♦) depicts the steady shear rate sweep of an alginate solution without calcium ions (alginate solution formulation #1 of Table 1).

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein In embodiments, the present disclosure is directed to cross-linked shear-thinning fluids of pectic acid displaying increased viscosity with decreasing shear, as well as methods of producing and using the same. A fluid is "shear-thinning" if the fluid viscosity decreases with increasing shear stress. As shown in FIG. 2, without the addition of a divalent cation, a pectic acid solution (pectic acid solution formulation #1 of Table 1) is a low viscous Newtonian fluid. This pectic acid solution had a viscosity around 13 mPa*s at a low shear rate of 1 s$^{-1}$, and demonstrated no clear change of viscosty with the application of increased shear rate. The present inventors discovered that an aqueous solution of pectic acid can be minimally cross-linked with low concentrations of a divalent cation, and this serves to increase the viscosity of the fluid and form a stable, non-Newtonian fluid with shear-thinning behavior (FIG. 2). After adding a small quantity of Ca$^{2+}$ (5 mM) to the aqueous solution of pectic acid, the minimally cross-linked pectic acid solution (pectic acid solution formulation #2 of Table 1) demonstrated a viscosity of roughly 20,800 mPa*s at a low shear rate of 1 s$^{-1}$; a 1600× increase in viscosity as compared to the pectic acid solution without the addition of a divalent cation (pectic acid solution formulation #1 of Table 1) (FIG. 2). Furthermore, the minimally cross-linked pectic acid solution demonstrated a higher viscosity as compared to a similarly prepared alginate solution (alginate solution formulation #2 of Table 1). While the minimally cross-linked pectic acid solution (pectic acid solution formulation #2 of Table 1) demonstrated a viscosity of roughly 20,800 mPa*s at a low shear rate of 1 s$^{-1}$, the similarly prepared alginate solution (alginate solution formulation #2 of Table 1) demonstrated a viscosity of roughly 8,100 mPa*s at a low shear rate of 1 s$^{-1}$. Unexpectedly, the minimally cross-linked shear-thinning fluid of pectic acid also displayed an increased shear-thinning response compared to the similarly prepared alginate solution, as demonstrated by the steeper negative slope of the minimally cross-linked pectic acid solution (pectic acid solution formulation #2 of Table 1) compared to the negative slope of the similarly prepared alginate solution (alginate solution formulation #2 of Table 1) (FIG. 2). More specifically, the viscosity of the minimally cross-linked pectic acid solution (pectic acid solution formulation #2 of Table 1) demonstrated a reduction from roughly 20,800 mPa*s to roughly 130 mPa*s (roughly a 1/160 reduction) when the shear rate was increased from 1 to 1000 s$^{-1}$ In contrast, the similarly prepared alginate solution (alginate solution formulation #2 of Table 1) demonstrated a reduction from roughly 8,100 mPa*s to roughly 256 mPa*s (roughly a 1/31 reduction) when the shear rate was increased from 1 to 1000 s$^{-1}$. Furthermore, the viscosity of the minimally cross-linked pectic acid solution (pectic acid solution formulation #2 of Table 1) became lower than even the alginate solution with no cross-linking (alginate solution formulation #1 of Table 1) when the shear rate was increased above 50 s$^{-1}$ (FIG. 2).

Figure 4:
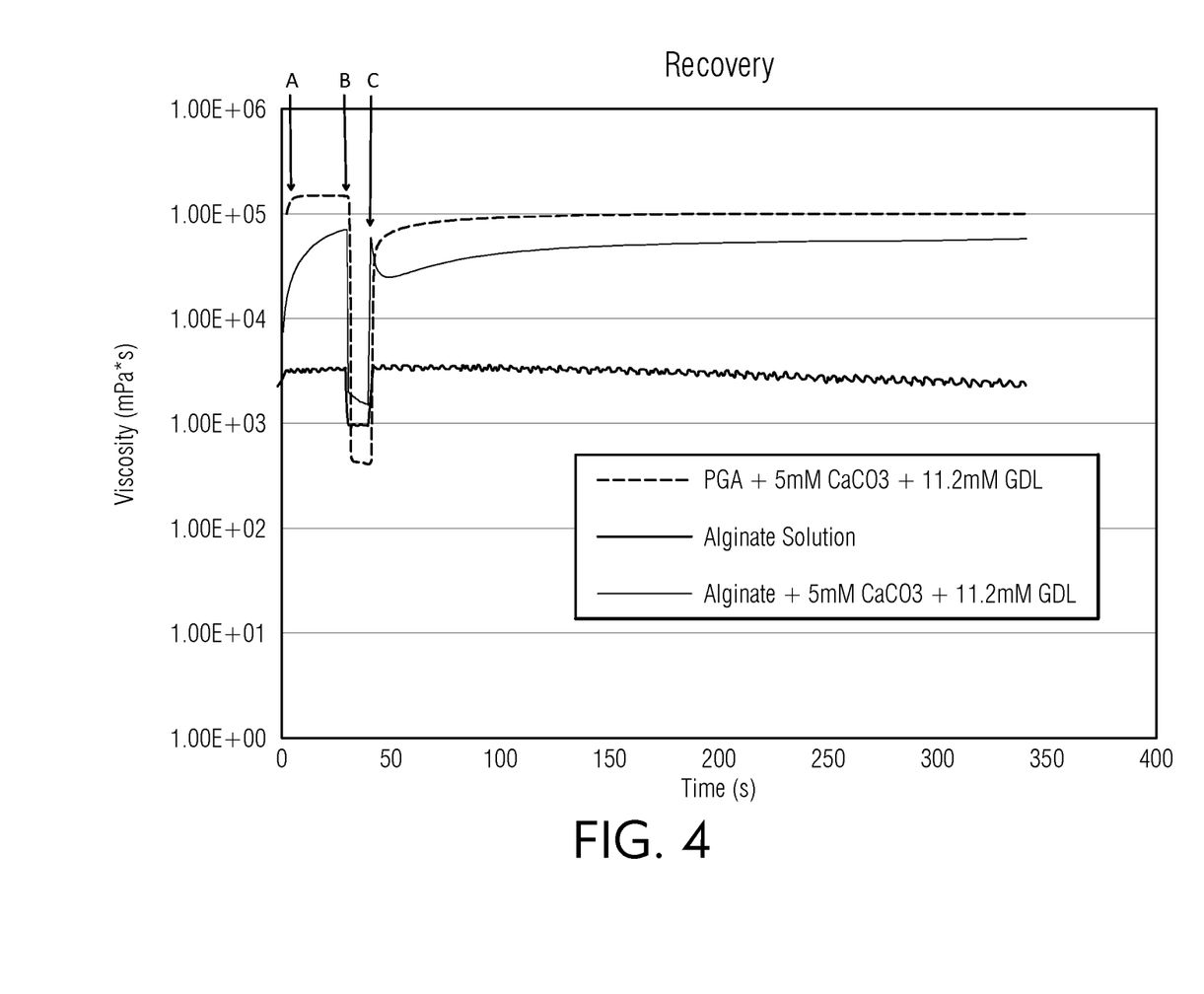
FIG. 4 is a graph depicting the results of a recovery test of alginate solutions with or without a low concentration of calcium ions and a pectic acid based solution with low concentration of calcium ions. Due to the Newtonian fluid nature of the pectic acid solution without calcium ions, it was not included in the test. The alginate solutions and pectic acid solutions were initially exposed to a low shear rate of 0.1 (Point A) for 30 seconds, and subsequently to a high shear rate of 100 $s^{-1}$ (Point B) for 10 seconds. The shear rate was then returned back to a low shear rate of 0.1 $s^{-1}$ (Point C). Recovery was determined after the high shear rate (100 $s^{-1}$) was removed. The heavy dark line depicts an alginate solution without calcium ions (alginate solution formulation #1 of Tale 1). The light line depicts an alginate solution containing 5 mM $CaCO_3$ and 11.2 mM of glucono-delta-lactone (alginate solution formulation #2 of Table 1). The dashed line depicts a pectic acid solution containing 5 mM $CaCO_3$ and 11.2 mM glucono-delta-lactone (pectic acid solution formulation #2 of Table 1).

As shown in FIG. 4, the minimally cross-linked shear-thinning fluids of pectic acid (pectic acid solution formulation #2 of Table 1) display increased viscosity with decreasing shear, and demonstrate rapid recovery back into stable, highly viscous fluids upon shear stress removal (FIG. 4). This recovery of strength from shear may be complete with minutes or even seconds. Surprisingly, the cross-linked shear-thinning fluids of pectic acid displayed higher and faster recovery responses than similarly prepared alginate solutions (FIG. 4). At a low shear rate of 0.1 s$^{-1}$ (point A in FIG. 4), the minimally cross-linked pectic acid solution (pectic acid solution formulation #2 of Table 1) demonstrated a higher viscosity than both the corresponding alginate solution (alginate solution formulation #2 of Table 1) and the alginate solution without cross-linking (alginate solution formulation #1 of Table 1). After exposure to a higher shear rate of 100 s$^{-1}$ (Point B in FIG. 4), the viscosity of the minimally cross-linked pectic acid solution (pectic acid solution formulation #2 of Table 1) was reduced by 350× as compared to exposure at a low shear rate (0.1 s$^{-1}$). Furthermore, after exposure to the higher shear rate (100 s$^{-1}$), the viscosity of the minimally cross-linked pectic acid solution (pectic acid solution formulation #2 of Table 1) demonstrated a lower viscosity than both the corresponding alginate solution (alginate solution formulation #2 of Table 1) and the alginate solution without cross-linking (alginate solution formulation #1 of Table 1) after exposure to the higher shear rate (100 s$^{-1}$). These results agree with the steady state shear rate sweep test shown in FIG. 2 and confirm the better shear-thinning properties of the minimally cross-linked pectic acid fluid. Additionally, during recovery after the high shear was removed (point C in FIG. 4), the viscosity of the minimally cross-linked pectic acid solution (pectic acid solution formulation #2 of Table 1) recovered quickly and reached 50% of its original viscosity in 2 seconds and roughly 70% of its original viscosity in 10 seconds (FIG. 4). In less than 2 seconds, the viscosity of the minimally cross-linked pectic acid solution (pectic acid solution formulation #2 of Table 1) had already increased to higher levels than both the corresponding alginate solution (alginate solution formulation #2 of Table 1) and the alginate solution without cross-linking (alginate solution formulation #1 of Table 1). Within 10 seconds, the viscosity of the minimally cross-linked pectic acid solution (pectic acid solution formulation #2 of Table 1) was already 3× the viscosity of the corresponding alginate solution (alginate solution formulation #2 of Table 1). Thus, the data in FIG. 4 confirms that the minimally cross-linked pectic acid solution display an increased shear-thinning response compared to the similarly prepared alginate solution, and further demonstrates that the minimally cross-linked pectic acid solution display higher and faster recovery responses than the similarly prepared alginate solution upon shear stress removal (FIG. 4).

Figure 3:
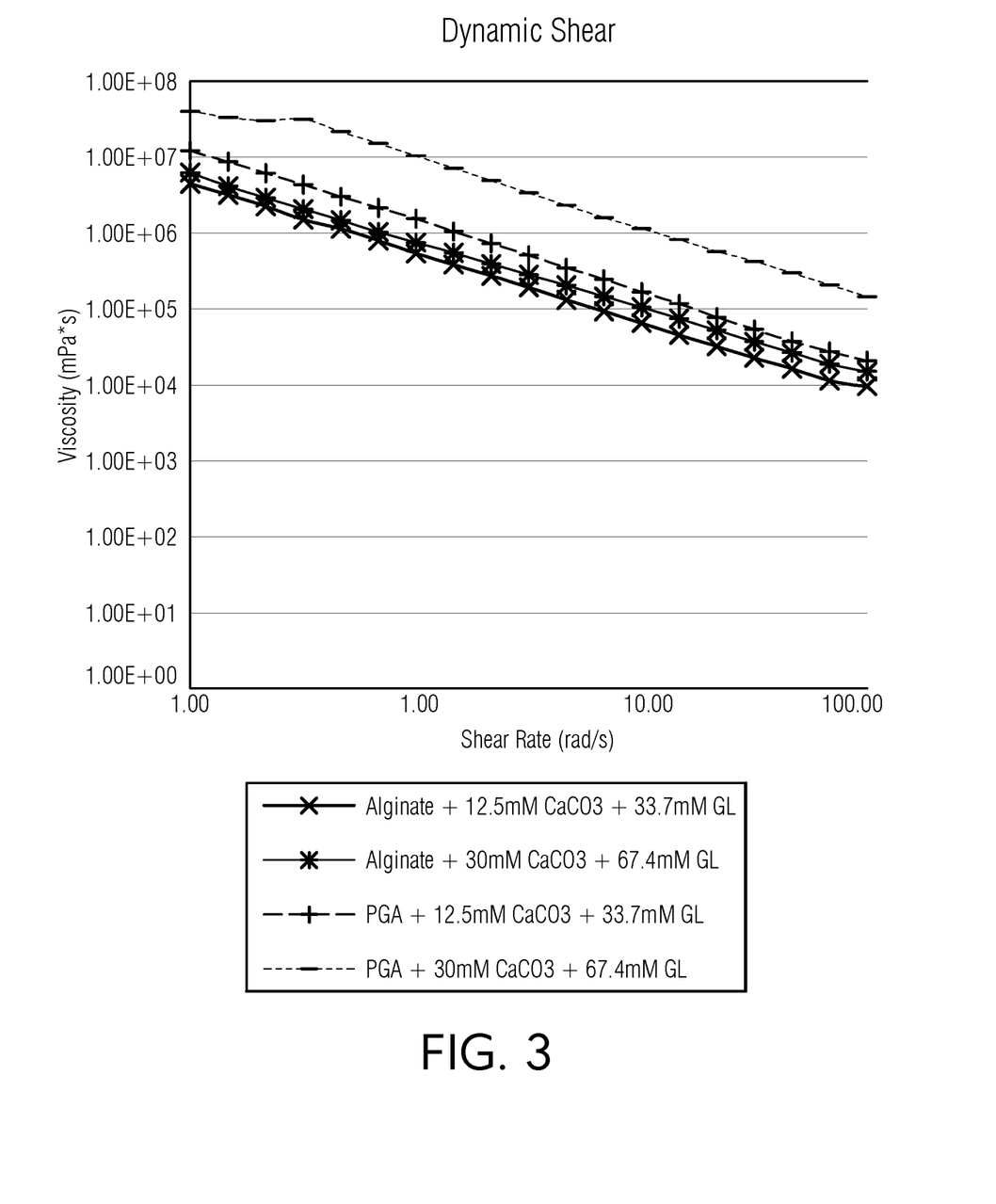
FIG. 3 is a graph depicting the results of dynamic shear rate sweeps of alginate or pectic acid based hydrogels having higher concentrations of calcium ions. (x) depicts the dynamic shear rate sweep of an alginate solution with 12.5 mM $CaCO_3$ and 33.7 mM of glucono-delta-lactone (alginate solution formulation #3 of Table 1). (*) depicts the dynamic shear rate sweep of an alginate solution containing 30 mM $CaCO_3$ and 67.4 mM of glucono-delta-lactone (alginate solution formulation #4 of Table 1). (+) depicts the dynamic shear rate sweep of a pectic acid solution with 12.5 mM $CaCO_3$ and 33.7 mM of glucono-delta-lactone (pectic acid solution formulation #3 of Table 1). (−) depicts the dynamic shear rate sweep of a pectic acid solution containing 30 mM $CaCO_3$ and 67.4 mM of glucono-delta-lactone (pectic acid solution formulation #4 of Table 1).

As shown in FIG. 3, the stable, cross-linked shear-thinning fluids of pectic acid can be further cross-linked by additional amounts of a divalent cation to form hydrogels that demonstrate higher viscosity than similarly prepared alginate hydrogels. Furthermore, these pectic acid hydrogels can be dissolved by low concentrations of pectinase and EDTA in a cell compatible environment, and may be dissolved one and a half time faster than similarly prepared alginate hydrogels (data not shown).

As such, the presently-disclosed cross-linked, shear-thinning fluids of pectic acid can be advantageously utilized for controlled release formulations, cell encapsulation, and 3D printing. Such cross-linked, shear-thinning fluids of pectic acid can provide for an improved balance between structure fidelity/mechanical stability and cell viability. These materials provide a highly viscous, stable fluid with improved shape fidelity and mechanical stability to encapsulate a therapeutic agent or cells in consistent and controlled conditions. Due to the high shear-thinning responses of this highly viscous and stable fluid, these materials can be delivered via injection, catheter, or from the head of a printer during 3D printing with improved cell viability. Importantly, the cross-linked shear-thinning fluids of pectic acid can rapidly recover back to a highly viscous, stable fluid at the target site after delivery, allowing for improved stability after injection and improved control of the geometry and the cellular and matrix composition of a printed structure after 3D printing. Furthermore, the cross-linked, shear-thinning fluids of pectic acid can be further cross-linked after such delivery to provide a surprisingly strong hydrogel as compared to similarly prepared and tested alginate hydrogels. For example, the cross-linked, shear-thinning fluids of pectic acid may be further crosslinked into a hydrogel after injection into the body through contact with additional sources of a divalent cation, such as calcium ions present in bodily fluids. Additionally, the cross-linked, shear-thinning fluids of pectic acid can be further cross-linked into a hydrogel after 3D printing by supplying additional divalent cations to the fluid. Thus, the rheological properties of the cross-linked, shear-thinning fluids of pectic acid can be fine-tuned by adjusting the amount of divalent cations added to fluid to provide for highly viscous fluids with better shear thinning and recovery properties than similarly prepared alginate based materials, and can therefore be utilized in various injection and 3D printing conditions.

In embodiments, a cross-linked, shear-thinning fluid comprising pectic acid is disclosed. In some embodiments, the shear-thinning fluid includes an aqueous solution, with the aqueous solution comprising pectic acid or a salt thereof cross-linked by divalent cations. Pectic acid, also known as polygalacturonic acid (PGA), are pectic substances that are mostly composed of colloidal polygalacturonic acids and are essentially free from or have no methyl ester groups. Pectic acid can be formed from the hydrolysis of certain esters of pectins. Pectins are cell wall polysaccharides which have a structural role in plants. They are predominantly linear polymers based on a 1,4-linked alpha-D-galacturonate backbone, interrupted randomly by 1,2-linked L-rhamnose. The average molecular weight may be from about 50,0000 to about 200,000 Daltons. The totally de-esterified pectin is pectic acid or PGA.

Two major sources of pectins are, for example, from citrus peel (mostly lemon and lime) or apple peels, and can be obtained from extraction thereof. However, besides citrus and apples, pectin has been obtained from potatoes, grape fruits, sugar beets and sunflower heads.

In embodiments, the pectic acid is present in the aqueous solution in an amount ranging from about 0.5 to about 3.0% (w/v), including any value or range therebetween. In other embodiments, the pectic acid is present in the aqueous solution in an amount ranging from about 1.0 to about 2.5% (w/v), including any value or range therebetween. In further embodiments, the pectic acid is present in the aqueous solution in an amount of about 1.6% (w/v).

In embodiments, the pectic acid may be a pectic acid sodium salt, a pectic acid potassium salt, a pectic acid magnesium salt, and/or pectic acid ammonium salt.

In embodiments, the pectic acid of the aqueous solution is minimally cross-linked with low concentrations of a multivalent cation to increase the viscosity of the fluid to form a stable, non-Newtonian fluid with shear-thinning behavior. Cross-linking of the pectic acid is preferably performed by ionic crosslinking, which is based on the ability of the pectic aid to crosslink in the presence of multivalent counter ions. The increase in the pectic acid fluid viscosity results from the strong interactions between multivalent cations and blocks of galacturonic residues. Without the addition of a multivalent cation, pectic acid solution is a low viscous Newtonian fluid. However, when minimally cross-linked with low concentrations of a divalent cation as disclosed herein, the viscosity of the fluid is substantially increased and forms a stable, non-Newtonian fluid with shear-thinning behavior (FIG. 2). Unexpectedly, the cross-linked shear-thinning fluids of pectic acid displayed higher responses to shear thinning than similarly prepared alginate solutions (FIG. 2).

In some embodiments, the pectic acid of the aqueous solution is uniformly cross-linked. Uniformly crosslinked is used herein to refer to the crosslinks being spread in a substantially non-clustered distribution, which may be a random distribution or an even distribution. Uniform cross-linking can be achieved, by way of example and not limitation, by internal crosslinking/gelation method. Additionally, uniform crosslinking can be achieved using a device that is capable of rigorously mixing the solution without substantially shearing the cross-linked pectic acid. Such a device can be a homogenizer, with a working speed preferably in the range of between about 5,000 and 50,000 rpm, including any value and range there between. Homogenization can be conducted for 30 seconds to 5 minutes, including any value and range there between.

Thus, the cross-linked shear-thinning fluids of pectic acid displaying increased viscosity with decreasing shear can be obtained by crosslinking, or uniformly crosslinking, the pectic acid of the aqueous solution with low concentrations of multivalent cations (e.g. divalent cations) present in the aqueous solution. The crosslinking can be achieved by providing an aqueous solution comprising pectic acid and divalent cations, and mixing said aqueous solution under conditions suitable for cross-linking the pectic acid with the divalent cations to thereby produce the shear-thinning fluid, wherein said shear-thinning fluid displays increased viscosity with decreasing shear.

By way of example and not limitation, the pectic acid may be cross-linked by internal ionic gelation. Internal gelation involves an aqueous solution of pectic acid containing a water insoluble divalent salt, such as a water insoluble calcium salt. The use of a water insoluble calcium salt allows for uniform dispersing within the pectic acid solution without causing non-uniform crosslinking during dispersing. Crosslinking is initiated by the addition of an acid to reduce the pH of the pectic acid solution and release soluble divalent cations form the insoluble salt. By way of example and not limitation, in embodiments such an acid may be a glacial acetic acid or a glucono-delta-lactone solution, which are slow release acids. Although termed internal gelation or internal ionic gelation, the pectic acid of the aqueous solution is minimally cross-linked with low concentrations of a multivalent cation to produce the highly viscous, cross-linked shear-thinning fluids of pectic acid disclosed herein.

In embodiments, the pectic acid is cross-linked by a divalent cation. In some embodiments, a divalent cation is present in the aqueous solution at a concentration of from about 0.5 mM to about 7.0 mM, including any value or range there between. In other embodiments, the divalent cation is present in the aqueous solution at a concentration of from about 2.5 mM to about 6.0 mM, including any value or range there between. In further embodiments, the divalent cation is present in the aqueous solution at a concentration of about 5 mM. Divalent cations for crosslinking the pectic acid include, but are not limited to, calcium, strontium, barium, zinc, and magnesium. In certain embodiments, the divalent cation is a calcium cation, which is an insolubilizing cation that is widely used as a crosslinking agent.

In some embodiments, the divalent cation is a cation salt. A divalent calcium cation salt can be a pharmacologically acceptable calcium salt, such as but not limited to, calcium oxalate, calcium tartrate, calcium phosphate, calcium carbonate, calcium sulfate, calcium gluconate and calcium citrate. In certain embodiments, the calcium salt is a water insoluble calcium salt. However, the ionic cross-linking of the pectic acid can also be achieved by using the salt of a divalent metal, such as magnesium, strontium, zinc, barium, other like cations, or combinations thereof.

The cross-linked shear-thinning fluids of pectic acid display increasing viscosity with decreasing shear, and demonstrate rapid recovery back into stable, high viscous fluids upon shear stress removal (FIG. 4). Upon removal of the mechanical shear force, the original fluid recovers to a viscous state that is the same as, or close to, its pre-shear state. In some embodiments, this recovery from shear may be complete within minutes or even seconds. Surprisingly, the cross-linked shear-thinning fluids of pectic acid displayed higher recovery responses than similarly prepared alginate solutions (FIG. 4). The stable, cross-linked shear-thinning fluids of pectic acid can be further cross-linked by additional amounts of a divalent cation to form a hydrogel that has a higher viscosity than a similarly prepared alginate hydrogel (FIG. 3). Thus, the rheological properties of the cross-linked, shear-thinning fluids of pectic acid can be fine-tuned by adjusting the amount of divalent cation added to the pectic acid fluid to provide for high viscous fluids with better shear thinning and recovery properties than alginate based materials. By providing for an improved balance between structure fidelity/mechanical stability and cell viability due to a high shear-thinning response, such materials can be utilized for vehicles for cell encapsulation and delivery, sustained or controlled release drug delivery systems, and cell containing material or cell containing scaffolds in tissue engineering, e.g., produced by 3D printing.

As such, embodiments of the cross-linked shear-thinning fluid of pectic acid further comprise a cell and/or an active agent. In embodiments, the cell and/or active agent can be included in the aqueous solution. In embodiments, the cells and/or active agent can be added to the aqueous solution before, during, and/or after cross-linking of the aqueous pectic acid solution and before the cross-linked shear-thinning fluids of pectic acid are injected or printed/deposited onto a substrate during 3D printing.

Non-limiting examples of cell types, including mammalian cell types, that can be included in the cross-linked shear-thinning fluids of pectic acid described herein include but are not limited to: smooth muscle cells, skeletal muscle cells, cardiac muscle cells, epithelial cells, endothelial cells, myoblasts, fibroblasts, embryonic stem cells, mesenchymal stem cells, induced pluripotent stem cells, differentiated stem cells, tissue-derived cells, and any combinations thereof. Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric), derived from an established cell strain or cell line, or can be cells that have undergone genetic engineering and/or manipulation to achieve a desired genotype of phenotype.

In some embodiments, cells can be obtained from a suitable donor, either human or animal, or from a subject into which the cells are to be implanted. Cells may be harvested from a donor using standard biopsy techniques known in the art Mammalian species include, but are not limited to, humans, monkeys, dogs, cows, horses, pigs, sheep, goats, cats, mice, rabbits, rats. In one embodiment, the cells are human cells. In other embodiments, the cells can be derived from animals such as, dogs, cats, horses, monkeys, or any other mammal.

Additional sources of human cells include, but are not limited to, mesenchymal stem cells (MSCs). MSCs are attractive for regenerative medicine purposes as they can be isolated from patients and readily expanded for use as an autograft tissue replacement. Unlike donor allografts, recipient-derived MSC autografts have zero risk of inter-person disease transmission or immune-mediated tissue rejection. An additional advantage of MSCs is that the crucial factors for settlement and subsequent differentiation of MSCs into skeletal muscle cells have been identified.

In some embodiments, one or more active agents can be included in the cross-linked shear-thinning fluids of pectic acid. Any suitable active agent (e.g., in an amount to facilitate the growth or differentiation of cells or to treat a disease or disorder) can be used. Examples include, but are not limited to, transforming growth factor-alpha (TGF-alpha), transforming growth factor-beta (TGF-beta), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor. Stromal-derived factor (SDF), peptides such as substance P (SP), agrin, small molecules such as adenosine, and combinations thereof.

Other suitable active agents that may be included in the cross-linked shear-thinning fluids of pectic acid can include, for example and not by way of limitation, a pharmacologically active substance; a small molecule, such as an inorganic compound, an organic compound and its salt thereof; a diagnostic agent; a therapeutic agent; a nucleic acid; a peptide; a polymer; a small protein; a large protein; and combinations thereof. A pharmacologically active substance includes a substance that illicits immune response, such as a vaccine. Examples of active agents include anti-bacterial agents, antimicrobial agents, antiparasitic agents, antibiotics, antihistamines, decongestants, antimetabolites, antiglaucoma agents, anti-cancer agents, antiviral agents, anti-fungal agents, anti-inflammatory agents, anti-diabetic agents, anesthetic agents, anti-depressant agents, analgesics, anti-coagulants, ophthalmic agents, angiogenic factors, immunosuppressants, anti-allergic agents, and combinations thereof. The amount of the active agent used would depend on the type, form, and nature of the active agent.

Therefore, embodiments provide methods of preparing a controlled or sustained release formulation of a cell and/or therapeutic agent in a subject, each method comprising introducing into the patient a composition comprising a cross-linked, shear-thinning fluid comprising pectic acid as described herein, and a cell, therapeutic agent, or combination thereof. Further embodiments include the addition of a carrier or excipient. A carrier may include any pharmaceutically acceptable carrier, such as water, saline, a buffered aqueous solution, a wetting agent, emulsion, tablet, and capsule, as are known in the art. The amount of carrier present depends on the cells and/or therapeutic agent used and the manner in which the formulation is to be delivered Following deposition within a body, such as e.g. by injection with a surgical needle or by deliver through a catheter, the cross-linked shear-thinning fluids of pectic acid as described herein may be further cross-linked by divalent cations in vivo to form a hydrogel. Without being bound by theory, it is believed that the calcium ions in bodily fluid, such as blood, can result in additional cross-linking in vivo to form a hydrogel. Once gelanized, the pectic acid material would provide even further mechanical support.

Further embodiments provide methods of printing a 3D structure, the method comprising providing a 3D printer or 3D printing system and the cross-linked, shear-thinning fluid comprising pectic acid as described herein. The method comprises the use of a 3D printer or 3D printing system, as are known in the art. For example, a 3D printer or 3D printing system may comprise: a print head, which can be a microfluidic liquid handling device comprising one or more microfluidic channels for receiving and directing materials to be dispensed, fluidic switches corresponding to the microfluidic channels for regulating flow of the materials to be printed, and a single orifice for dispensing the materials to be dispensed. The 3D printer or 3D printing system may comprise: a receiving surface for receiving material dispensed by the print head; and a positioning unit operably coupled to the receiving surface, the positioning unit for positioning the print head at a location in three dimensional space above the receiving surface.

Figure 5:
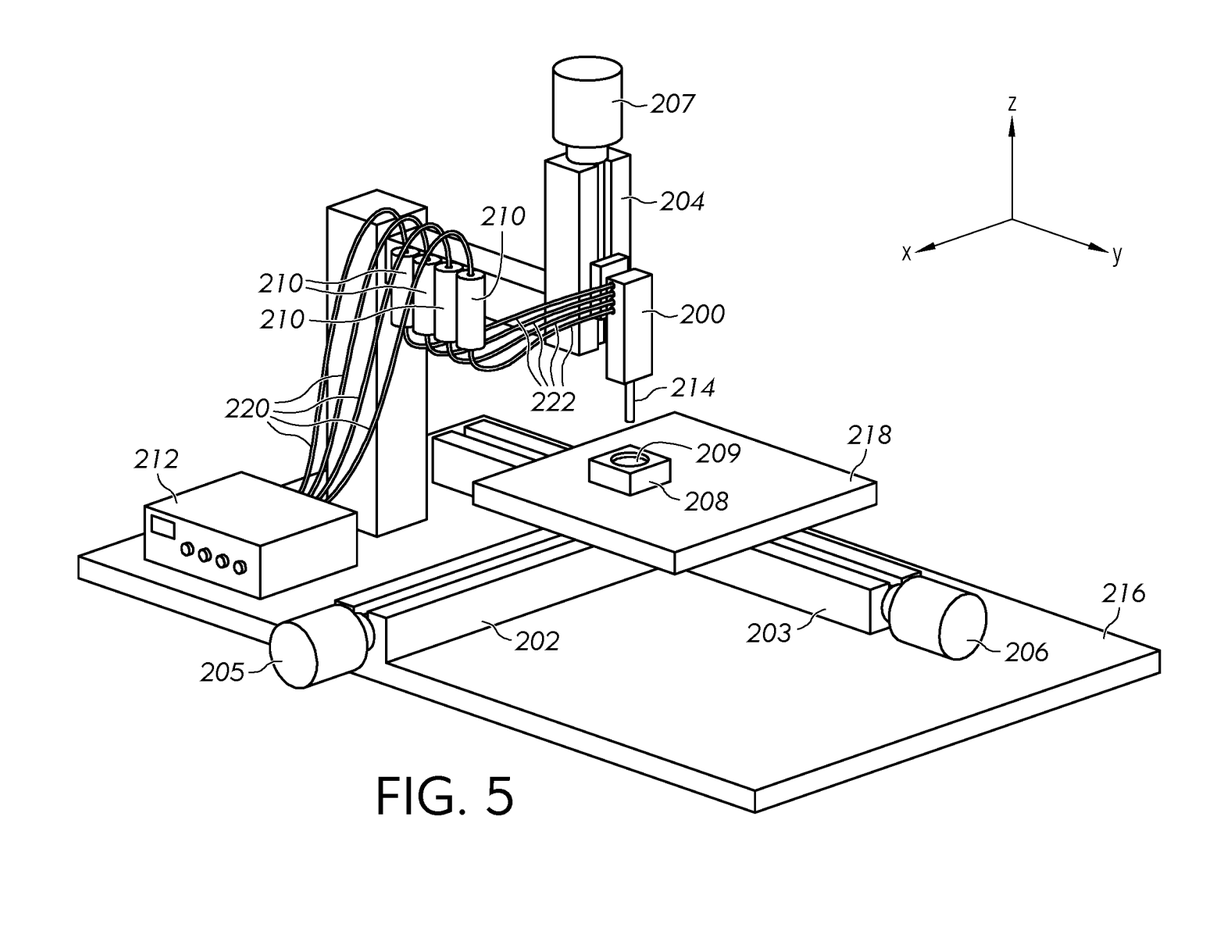
FIG. 5 is a schematic illustration of an embodiment of a 3-D printing system for use with embodiments of the cross-linked shear-thinning fluids of pectic acid disclosed herein.

FIG. 5 depicts a schematic perspective of an exemplary 3D printing system. The 3D printing system of FIG. 5 comprises a microfluidic print head 200. The print head 200 comprises at least one print head orifice 214 and at least one inlet for receiving material to be dispensed from the print head 200. In aspects of the method of printing a 3D structure, the material to be dispensed from the print head 200 comprises the cross-linked, shear-thinning fluid comprising pectic acid as described herein. In aspects, the cross-linked, shear-thinning fluid comprising pectic acid further comprises at least a cell. In further aspects, the materials to be dispensed from the print head can further include a sheath fluid. A "sheath fluid" is a liquid that is used, at least in part, to envelope or sheath a material to be dispensed, such as the cross-linked, shear-thinning fluid comprising pectic acid as disclosed herein. In aspects, the sheath fluid comprises a chemical cross-linking agent suitable for further solidifying the cross-linked, shear-thinning fluid comprising pectic acid as described herein to a solid hydrogel. Suitable cross-linking agents are as described previously, and include but are not limited to divalent cations, divalent cation salts, and water insoluble calcium salts. In aspects, the sheath fluid comprising a chemical cross-linking agent can further comprise an aqueous solvent, such as water or glycerol. In further aspects, the materials to be dispensed from the print head 200 can further include a structural support polymer used to form a 3D scaffold, as described in more detail below. In embodiments, the print head 200 may be configured to receive and dispense two or more materials to be dispensed from the print head 200. For example, the print head 200 can include more than one print head orifice 214, so that the print head 200 can dispense the shear-thinning fluid comprising pectic acid (and in certain aspect further comprising at least a cell), a sheath fluid comprising a chemical cross-linking agent suitable for further solidifying the cross-linked shear-thinning fluid comprising pectic acid while or immediately after it is dispensed, and/or a structural support polymer that is used to form a 3D scaffold of the printed 3D structure.

The materials to be dispensed are stored in printed material reservoirs 210 and delivered to the print head through respective first connecting tubes 222, which provide fluid communication between the print head 200 and the printed material reservoirs 210. In the illustrated embodiment, the means for dispensing the material from the print head orifice is a pressure control unit 212, which is fluidly coupled to the printed material reservoirs 210 by respective second connecting tubes 220. As is known in the art, the pressure control unit 212 is a means for providing a force to dispense the materials to be dispensed, and forces fluid out of the reservoirs 210 and into the print head 200 via respective first connecting tubes 222. The pressure control unit 212 supplies pressure to the printed material reservoirs 210 via respective second connecting tubes 220. However, it should be understood that alternative means for dispensing the material to be dispensed could be used in the illustrated embodiment. For example, a series of electronically controlled syringe pumps could be used to provide force for dispensing the material from the print head orifice.

Still referring to FIG. 5, the microfluidic print head 200 is coupled to a positioning system as are known in the art. An exemplary positioning system includes a 3D motorized stage comprising three arms (202, 203 and 204) for positioning the print head 200 and the print head orifice 214 in three dimensional space above a print bed 208, which comprises a surface 209 for receiving printed material. The 3D motorized stage can be controlled to position a vertical arm 204, which extends along the z-axis of the 3D motorized stage such that the print head orifice 214 is directed downward. A first horizontal arm 202 extends along the x-axis of the motorized stage and is secured to an immobile base platform 216. A second horizontal arm 203, extends along the y-axis of the motorized stage and is moveably coupled to an upper surface of the first horizontal arm 202 such that the longitudinal directions of the first and second horizontal arms 202 and 203 are perpendicular to one another. The terms "vertical" and "horizontal" as used herein with respect to the arms are meant to describe the manner in which the print head is moved and do not necessarily limit the physical orientation of the arms themselves.

Still referring to the exemplary 3D printing system of FIG. 5, the print-bed 208 is positioned on top of a platform 218. The platform 218 is coupled to an upper surface of the second horizontal arm 203. The 3D motorized stage arms (202, 203, and 204) are driven by three corresponding motors (205, 206 and 207), respectively, and controlled by a programmable control processor, such as a computer. In aspects, the print head 200 and print-bed 208 are collectively moveable along all three primary axes of a cartesian coordinate system by the 3D motorized stage and movement of the stage is defined using computer software.

Still referring to the exemplary 3D printing system of FIG. 5, as a material is dispensed from the print head orifice 214 (e.g. the cross-linked, shear-thinning fluid comprising pectic acid (optionally containing a cell), a sheath fluid, and/or a polymer that is used to form a 3D scaffold of the printed 3D structure), the positioning unit is moved in a pattern controlled by software, thereby creating a layer of the dispensed material on the receiving surface 209. Additional layers of dispensed material are stacked on top of one another such that the final 3D structure of the dispensed layers of material is generally a replica of the 3D geometry design provided by the software. The 3D design may be created using typical 3D CAD (computer aided design) software or generated from digital images, as known in the art. Further, it is possible to assign a specific material type to different geometrical locations within the 3D printed structure, including within layers, between layers, or both within and between layers, in any desired shape or pattern.

Due to its high shear-thinning response and rapid recovery, the instantly disclosed cross-linked, shear-thinning fluid comprising pectic acid may be used for the direct printing of cellular materials. Thus, in some embodiments, the cross-linked, shear-thinning fluid comprising pectic acid can further include a cell, a therapeutic agent, or combination thereof as previously described. In aspects, the cross-linked, shear thinning fluid may be used as a cell containing structure contained within a 3D scaffold. A 3D scaffold serves to provide a frame to support and protect the cell containing structure (e.g., the cell containing structure of cross-linked, shear-thinning fluid comprising pectic acid) from external loads or disruption. In aspects, a 3D scaffold comprises a polymer that provides structural support, as described below. In further aspects, the cross-linked, shear-thinning fluid comprising pectic acid can serve as a cell containing 3D structural scaffold itself. In even further aspects, the cross-linked, shear-thinning fluid comprising pectic acid can be used as a sacrificial material within a 3D structure. A "sacrificial material" is a material that is eventually removed from the printed 3D structure. A sacrificial material may serve to temporarily support adjacent deposited cell-containing materials that would otherwise collapse or fail to hold their printed shape during fabrication due to the low mechanical strength of the cell containing material. In additional embodiments, the cross-linked shear thinning fluid of pectic acid (with or without the addition of a cell, therapeutic agent, or combination thereof) may be printed and subsequently or simultaneously further contacted with a sheath fluid that contains additional multivalent cations, as previously described. Such a sheath fluid containing additional multivalent cations may be provided as a solution containing calcium cations, and can be added to the cross-linked shear thinning fluid of pectic acid simultaneously or after dispensation from the print head 200 of the 3D printer. For example, a print head 200 can include more than one print head orifice 214, so that the print head 200 can dispense the shear-thinning fluid comprising pectic acid (and in certain aspects further comprising at least a cell), and a sheath fluid comprising a chemical cross-linking agent suitable for further solidifying the cross-linked, shear-thinning fluid comprising pectic acid to a solid hydrogel during or immediately after it is dispensed from the print head 200. This additional cross-linking can be used to form a hydrogel to provide even further mechanical support to the cross-linked shear-thinning fluid comprising pectic acid, whether utilized as a cell containing structure within a 3D scaffold, the 3D scaffold itself, or as a sacrificial material within a 3D structure.

When the cross-linked shear-thinning fluid comprising pectic acid as described herein is used as a cell containing structure within a 3D scaffold or as a sacrificial polymer within a 3D printed structure, a polymer may be used to create the 3D scaffold of the 3D printed structure. Such polymers for the scaffold can be any suitable material that provide structural support to the 3D printed structure, including biodegradable or bioerodible materials, and materials that are stable or inert in vivo. Examples include, but are not limited to, poly(lactic acid) polymers, poly(glycolic acid) polymers, poly(lactide-co-glycolides), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactic acid, polyglycolic acids, nylons, polyamides, polyanhydrides, poly(ethylene-co-vinyl alcohol), polycaprolactone, poly(vinyl acetate), polyvinylhydroxide, poly(ethylene oxide), and polyorthoesters or a co-polymer formed from at least two members of the group. Additional examples of structural support polymers include, but are not limited to, other natural materials with chemical modification for chemical cross-linking or photo-chemical cross-linking. e.g. gelatin, fibrinogen, gellan gum, pluronics (poloxamers), alginate, chitosan, hyaluronic acid, cellulose, and collagen. The print head 200 can include more than one print head orifice 214 so that the print head 200 can dispense the shear-thinning fluid comprising pectic acid (and in certain aspects further comprising at least a cell), optionally a sheath fluid comprising a chemical cross-linking agent as described herein, and/or the polymer for forming the 3D scaffold.

In further embodiments, the cross-linked shear-thinning fluid comprising pectic acid as described herein can be used as a sacrificial material within a 3D printed structure. As previously described, a "sacrificial material" is a material that is eventually removed from the printed 3D structure. A sacrificial material may serve to temporarily support adjacent deposited cell-containing materials that would otherwise collapse or fail to hold their printed shape during fabrication due to the low mechanical strength of the cell containing material. When used as a sacrificial material, the cross-linked shear-thinning fluid comprising pectic acid as described herein can be dispended with or alongside the cell-containing structure (which can be a hydrogel or gel) and/or the 3D scaffold. The cross-linked shear-thinning fluid comprising pectic acid may be further cross-linked with additional multivalent cations, such as a solution containing calcium cations, before or upon dispensation form the print head of the 3D printer. This additional cross-linking can be used to form a hydrogel sacrificial material, which can provide even further mechanical support within the 3D printed structure up until the sacrificial material is removed from the 3D structure.

When used as a sacrificial material within a 3D structure, the cross-linked shear-thinning fluid is removed after hardening the dispensed 3D structure (for example, after cross-linking polymers in the cell carrier composition after deposition thereof or after the polymer of the 3D scaffold is fully hardened or solidified). A non-proteolytic enzyme, and optionally a chelating agent e.g., EDTA, suitable for digesting the pectic acid based sacrificial material can be utilized. Suitable non-proteolytic enzymes can include pectinolytic enzymes or pectinases, which are a heterogeneous group of related enzymes that hydrolyze the pectic substances, present mostly in plants. Pectinases (polygalacturonase) are enzymes that break down complex pectin molecules to shorter molecules of galacturonic acid. Pectinase catalyzes the liberation of pectic oligosaccharides (POS) from polygalacturonic acid. Pectinases are produced by fungi, yeast, bacteria, protozoa, insects, nematodes and plants. Commercially available sources of pectinases are generally multi-enzymatic, such as Novozyme Pectinex™ ULTRA SPL, a pectolytic enzyme preparation produced from a selected strain of *Aspergillus aculeatus*. It contains mainly polygalacturonase, (EC 3.2.1.15) pectintranseliminase EC 4.2.2.2) and pectinesterase (EC: 3.1.1.11). Pectinases are known to hydrolyze pectin. They may attack methyl-esterified pectin or de-esterified pectin. The EC designation and number is the Enzyme Commission classification scheme for enzymes based on the chemical reactions the enzymes catalyze.

As previously described, the 3D structure of the dispensed layers of materials from the 3D printing system is generally a replica of the 3D geometry design provided by the software, with such a 3D design typically created using typical 3D CAD (computer aided design) software or generated from digital images, as known in the art. Further, it is possible to assign a specific material type (e.g., the cell containing material, the sacrificial material, and/or the polymer of the 3D scaffold) to different geometrical locations within layers, between layers, or both within and between layers in any desired shape or pattern. Therefore, as a sacrificial material, the cross-linked shear-thinning fluid comprising pectic acid can be assigned and printed in specific geometrical locations within layers, between layers, or both within and between layers of the 3D printed structure in any desired shape or pattern. Thus, the cross-linked shear-thinning fluid comprising pectic acid can be printed such that removal of the sacrificial material from the hardened 3D structure creates openings, including pores, cavities, channels, lumens, etc. in the 3D printed composite structure. The openings can be used to carry nutrients into, waste from, or active compounds into or out of the composite. The openings can be in the form of a series of interconnecting pores interconnecting within layers, between layers, or both within and between layers. The openings can be elongate channels that branch to or from one another (e.g., as diverging branches, converging branches, or both diverging and then connected converging branches forming a capillary bed). The openings can be formed within layers, between layers, or both within and between layers of the 3D printed structure, as desired.

The foregoing description is illustrative of particular aspects of the present diclosure, but is a limitation upon the practice thereof. In order that various aspects may be more readily understood, reference is made to the following examples which are intended to illustrate various aspects, but do not limit the scope thereof.

EXAMPLES

The following examples are given by way of illustration and are in no way intended to limit the scope of the present disclosure.

Example 1

Materials and Methods

To provide uniform gelation or crosslinking for a pectic acid solution, we used an internal gelation method. In this method, calcium carbonate ($CaCO_3$) particles were dispersed into a pectic acid solution as an insoluble source for $Ca^{2+}$. Freshly made glucono-delta-lactone (GDL) solution was added into the above dispersion as a source of acid. The hydrolyzation of GDL slowly generated gluconic acid which reacted with calcium carbonate particles to release $Ca^{2+}$ and crosslink pectic acid molecules uniformly. All the samples were prepared 1 day before the rheology test to give enough time for the hydrolyzation of GDL and release of $Ca^{2+}$.

More specifically, pectic acid sodium salt solutions were mixed with different volumes of $CaCO_3$ suspension and freshly made GDL solution. The polymer concentrations in all the formulations were adjusted 1.6% using water. The concentrations of $CaCO_3$ and GDL in the obtained formulations were as shown in Table 1. A sodium alginate solution (the polymer concentration adjusted 1.6% using water) was mixed with the $CaCO_3$ suspension and GDL solution to introduce the same amounts of calcium ion for comparison.

TABLE 1

The concentrations of $CaCO_3$ and GDL in different formulations of pectic acid or alginate for rheology tests. The final polymer concentrations are 1.6% for both polymers.

| Formulation ID | $CaCO_3$ | GDL |
| --- | --- | --- |
| #1 | 0 mM | 0 mM |
| #2 | 5 mM | 11.2 mM |
| #3 | 12.5 mM | 33.7 mM |
| #4 | 30 mM | 67.4 mM |

Rheology properties of the formulations were tested using steady shear rate sweep from 1 to 1000 $s^{-1}$ or dynamic shear rate sweep from 0.1 to 100 $s^{-1}$. These tests are used demonstrate the different shear thinning response from the different formulations. To understand how the formulations are able to recover their strength after exposure to high shear, selected formulations were subjected to a recovery test. This test helped to demonstrate how well those formulations can maintain shape fidelity and mechanical stability after printing or injection. In this test, initial viscosity of the formulations was measured at a shear rate of 0.1 $s^{-1}$ for 30 seconds, and then the formulations were exposed to a high shear rate of 100 $s^{-1}$ for 10 seconds. Finally the shear rate was returned back to 0.1 $s^{-1}$ to monitor the recovery of viscosity with time.

To evaluate the capability of pectic acid and alginate based hydrogels to be used as a sacrificial material for 3D bioprinting, the obtained hydrogels were printed at a volume of 250 µl as grid like patterns and fully crosslinked using excessive $Ca^{2+}$. Before being subjected to a dissolution test, calcium free DPBS buffer was used to remove unbound $Ca^r$, and toluidine blue O (TBO) was used to stain the hydrogel structure for visualization. For dissolution, the hydrogel structures were exposed to 20 ml of a 5 mM EDTA and 50 U/ml Pectinase solution. The time required for dissolution of the structures was used to quantify how easily those materials can be removed if used as a sacrificial material.

Example 2

Results Limited Crosslinking

For formulation #1 and #2 of pectic acid and alginate polymers (Table 1), rheological properties were measured under steady shear, which is relevant during injection or extrusion during 3D printing. The obtained shear sweep results are shown in FIG. 2.

Referring to FIG. 2, the viscosity of formulation #1 of alginate solution (which contained no $Ca^{2\pm}$) was around 1350 mPa*s at shear rate of 1 $s^{-1}$ and started to reduce when shear rate was increased to higher than 10 $s^{-1}$ Finally, the viscosity was reduced to 256 mPa*s at shear rate of 1000 $s^{-1}$. As such, formulation #1 of alginate solution demonstrated some extent of shear thinning behavior. For formulation #2 of alginate solution, after introducing a small quantity of $Ca^{2+}$ (5 mM), its viscosity increased by 6 times at a shear rate of 1 $s^{-1}$ compared to formulation #1 of alginate, but continued to decrease with increased shear rate. The viscosity of formulation #2 of alginate solution, which included the addition of 5 mM of $Ca^{2+}$, became comparable to alginate solution without $Ca^{2+}$ (formulation #1) when the shear rate was higher than 100 Therefore, its response to shear thinning was increased.

Still referring to FIG. 2, formulation #1 of pectic acid solution (which contained no $Ca^n$) demonstrated a typical Newtonian fluid behavior with no clear change of viscosity when shear rate was increased. The viscosity formulation #1 of pectic acid solution was the lowest of all tested formulations and was about 13 mPa*s, which was 1/100 of the alginate solution of formulation #1. For formulation #2 of pectic acid solution, after adding a small quantity of $Ca^{2+}$ (5 mM) the material became a non-Newtonian fluid which showed a viscosity of 20810 mPa*s at low shear rate of 1 $s^{-1}$. This is a 1500× increase compared to formulation #1 of pectic acid solution. The viscosity was also much higher than the corresponding alginate solution at the same shear rate. Formulation #2 of pectic acid solution also demonstrated a higher shear thinning response than the corresponding alginate solution. Its viscosity was reduced to 130 mPa*s, a 1/150 reduction, when the shear rate was increased from 1 to 1000 s$^{-1}$. The viscosity of formulation #2 of pectic acid solution also became lower than even formulation #1 of alginate solution, which contained no Ca$^{2+}$, after the shear rate increased above 50 s$^{-1}$.

High Degree of Crosslinking

To evaluate the viscosity of the pectic acid and alginate formulations with further crosslinking, both polymer solutions were introduced with additional Ca$^{2+}$ by adding additional amounts of CaCO$_3$ and GDL (formulation #3 & #4 in Table 1). Formulation #3 for both pectic acid and alginate included 12.5 mM of Ca$^{2+}$, while formulation #4 for both pectic acid and alginate included 30 mM of Ca$^{2+}$. All of these formulations formed solid hydrogels which could not flow and were damaged during steady shear tests. Therefore, rheological properties of these formulations were measured using dynamic shear sweep. The results are shown in FIG. 3. Both formulation #3 and formulation #4 for pectic acid and alginate polymers showed similar shear-thinning trends in logarithmic scale. However, for alginate hydrogel formulations, there was limited increase in viscosity when Ca$^{2+}$ was increased from 12.5 mM in formulation #3 to 30 mM in formulation #4. Both formulation #3 and formulation #4 for pectic acid showed higher viscosity than either alginate formulations, and a greater increase in viscosity was observed in the pectic acid formulations when Ca$^{2+}$ was increased from 12.5 mM in formulation #3 to 30 mM in formulation #4 as compared to the alginate formulations #3 and #4.

Recovery Test

To evaluate how the fluid formulations of pectic acid and alginate (formulation #1 & #2) are able to recover their strength after exposed to high shear, these materials were subjected to a recovery test. Due to the Newtonian fluid nature of formulation #1 of pectic acid, it was not included in the test. The results of the recovery test are shown in FIG. 4. In this test, initial viscosity of the formulations was measured at a shear rate of 0.1 s$^{-1}$ for 30 seconds, and then the formulations were exposed to a high shear rate of 100 s$^{-1}$ for 10 seconds. Finally the shear rate was returned back to 0.1 s$^{-1}$ to monitor the recovery of viscosity with time. At low shear rate of 0.1 s$^{-1}$ (Point A in FIG. 4), formulation #2 of pectic acid with limited calcium (5 mM) had higher viscosity than the corresponding alginate formulation #2 with limited calcium (5 mM) or alginate solution alone without Ca$^{2+}$ (formulation #1). After exposure to a high shear of 100 s$^{-1}$ (Point B in FIG. 4), the viscosity of the pectic acid solution of formulation #2 was reduced by 350x lower than both alginate formulations tested. These results agree with the shear rate sweep test shown above in FIG. 2 and confirmed better shear-thinning property for the pectic acid based formulations. During recovery after the high shear was removed (Point C in FIG. 4), the viscosity of the pectic acid solution of formulation #2 recovered quickly and reached 50% of original viscosity in 2 seconds and about 70% of original viscosity in 10 seconds. In less than 2 seconds, its viscosity has already increased to higher than both tested alginate formulations at the same time point. After 10 seconds, its viscosity is almost 3x that of the corresponding alginate solution of formulation #2. There was a peak value in viscosity for alginate formulation #2 after the removal of high shear, which could be caused by some measurement artifact.

Dissolving of Printed Structures

Hydrogels of pectic acid or alginate were printed at a volume of 250 μl as grid like patterns and fully crosslinked using excessive Ca$^{2+}$ (67.4 mM). Before being subjected to a dissolution test, calcium free DPBS buffer was used to remove unbound Ca$^{2+}$, and toluidine blue O (TBO) was used to stain the hydrogel structure for visualization. For dissolution, the hydrogel structures were exposed to 20 ml of a 5 mM EDTA and 50 U/ml Pectinase solution. The time required for dissolution of the structures was used to quantify how easily those materials can be removed if used as a sacrificial material. The dissolving test demonstrated that the fully cross-linked pectic acid based hydrogel of formulation #4 dissolved in less than 1 hour while the alginate based hydrogel of formulation #4 maintained its structure at the same time point (data not shown). In fact, the alginate hydrogel required at least 1.5x the amount of time to completely dissolve (data not shown).

It will be appreciated by those skilled in the art that changes could be made to the embodiments described above without departing from the broad inventive concept thereof. It is understood, therefore, that this disclosure is not limited to the particular embodiments disclosed, but is intended to cover modifications that are within the spirit and scope of the disclosure, as defined by the appended claims.

What is claimed is:

1. A shear-thinning fluid comprising: an aqueous solution comprising pectic acid cross-linked by divalent cations, wherein the pectic acid is present in an amount ranging from about 0.5 to about 3.0% (w/v), wherein the divalent cations are present at a concentration of from about 0.5 mM to about 7.0 mM, and wherein the viscosity of the shear-thinning fluid increases with decreasing shear.

2. The shear-thinning fluid of claim 1, wherein the divalent cations are present at a concentration of from about 2.5 mM to about 6.0 mM.

3. The shear-thinning fluid of claim 1, wherein the divalent cations are present at a concentration of about 5 mM.

4. The shear-thinning fluid of claim 1, wherein the pectic acid is present in an amount of about 1.0 to about 2.5% (w/v).

5. The shear-thinning fluid of claim 1, wherein pectic acid is present in an amount of about 1.6% (w/v).

6. The shear-thinning fluid of claim 1, wherein the pectic acid is uniformly cross-linked.

7. The shear-thinning fluid of claim 1, wherein the pectic acid is a pectic acid sodium salt.

8. The shear-thinning fluid of claim 1, wherein the divalent cations are selected from the group consisting of calcium cations, magnesium cations, strontium cations, and barium cations.

9. The shear-thinning fluid of claim 8, wherein the divalent cations are calcium cations.

10. The shear-thinning fluid of claim 9, wherein the calcium cations are provided by a calcium salt.

11. The shear-thinning fluid of claim 10, wherein the calcium salt is selected from the group consisting of calcium oxalate, calcium tartrate, calcium phosphate, calcium carbonate, calcium sulfate, and calcium citrate.

12. The shear-thinning fluid of claim 1, wherein the aqueous solution further comprises cells and/or a therapeutic agent.

13. The shear-thinning fluid of claim 1, wherein the shear-thinning fluid comprises a viscosity of more than 20,000 mPa*s at a shear rate of 1 s$^{-1}$.

14. The shear-thinning fluid of claim 1, wherein the shear-thinning fluid comprises a viscosity of less than 150 mPa*s at a shear rate of 1000 s$^{-1}$.

15. The shear-thinning fluid of claim 1, wherein the shear-thinning fluid comprises a first viscosity at a low shear rate of 1 s$^{-1}$ and a second viscosity at a high shear rate of $1000 \text{ s}^{-1}$, the first viscosity being at least about two orders of magnitude greater than the second viscosity.

16. The shear-thinning fluid of claim 15, wherein the second viscosity is about $1/160^{th}$ of the first viscosity.

17. The shear-thinning fluid of claim 15, wherein the shear-thinning fluid comprises a third viscosity at a lower shear rate of $0.1 \text{ s}^{-1}$, the second viscosity begin about $1/350^{th}$ of the third viscosity.

18. The shear-thinning fluid of claim 1, wherein the viscosity of the shear-thinning fluid recovers to a viscous state that is the same as its pre-shear state to a viscous state that is the same as its pre-shear state.

19. The shear-thinning fluid of claim 1, wherein all of the divalent cations that cross-link between two polymer molecules cross-link from pectic acid to pectic acid.

\* \* \* \* \*